US011793493B2

(12) United States Patent
Takagi (10) Patent No.: US 11,793,493 B2
(45) Date of Patent: Oct. 24, 2023

(54) ULTRASOUND DIAGNOSTIC APPARATUS, CONTROL METHOD FOR ULTRASOUND DIAGNOSTIC APPARATUS, AND NON-TRANSITORY COMPUTER-READABLE RECORDING MEDIUM STORING CONTROL PROGRAM FOR ULTRASOUND DIAGNOSTIC APPARATUS

(71) Applicant: Konica Minolta, Inc., Tokyo (JP)

(72) Inventor: Kazuya Takagi, Tokyo (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days.

(21) Appl. No.: 17/201,612

(22) Filed: Mar. 15, 2021

(65) Prior Publication Data

US 2021/0298722 A1    Sep. 30, 2021

(30) Foreign Application Priority Data

Mar. 25, 2020    (JP) .................................. 2020-054307

(51) Int. Cl.
*A61B 8/00* (2006.01)
*A61B 8/08* (2006.01)
*A61B 5/00* (2006.01)

(52) U.S. Cl.
CPC .............. *A61B 8/5261* (2013.01); *A61B 8/08* (2013.01); *A61B 8/463* (2013.01); *A61B 8/5207* (2013.01); *A61B 8/54* (2013.01); *A61B 5/0077* (2013.01)

(58) Field of Classification Search
None
See application file for complete search history.

(56) References Cited

U.S. PATENT DOCUMENTS

| 2015/0164479 | A1* | 6/2015 | Toji | A61B 8/463 |
| | | | | 600/440 |
| 2021/0290107 | A1* | 9/2021 | Murray | H04W 4/38 |

FOREIGN PATENT DOCUMENTS

JP    2009-207800 A    9/2009

* cited by examiner

*Primary Examiner* — Colin T. Sakamoto
(74) *Attorney, Agent, or Firm* — LUCAS & MERCANTI, LLP (57) ABSTRACT

Provided is an ultrasound diagnostic apparatus to be applied to an ultrasound inspection of a living body part that moves with a movement of a subject in a living body inside the subject. The ultrasound diagnostic apparatus includes: an ultrasound image generation section that generates an ultrasound image based on a reception signal acquired from ultrasound probe which transmits and receives an ultrasound; an image analysis section that detects a movement of the subject by performing an image analysis of time-series camera images acquired from a camera which images the movement of the subject; and a display image generation section that generates a display image including the ultrasound image, and changes a display content or display mode of the display image in conjunction with the movement of the subject detected by the image analysis.

17 Claims, 11 Drawing Sheets

SUBJECT CHANGES MOVEMENT DIRECTION

ULTRASOUND DIAGNOSTIC APPARATUS, CONTROL METHOD FOR ULTRASOUND DIAGNOSTIC APPARATUS, AND NON-TRANSITORY COMPUTER-READABLE RECORDING MEDIUM STORING CONTROL PROGRAM FOR ULTRASOUND DIAGNOSTIC APPARATUS

CROSS REFERENCE TO RELATED APPLICATIONS

The entire disclosure of Japanese Patent Application No. 2020-054307 filed on Mar. 25, 2020 is incorporated herein by reference in its entirety.

BACKGROUND

Technological Field

The present invention relates to an ultrasound diagnostic apparatus, a control method for an ultrasound diagnostic apparatus, and a non-transitory computer-readable recording medium storing control program for an ultrasound diagnostic apparatus.

Description of Related Art

Conventionally, an ultrasound diagnostic apparatus has been known, which transmits an ultrasound into a subject, receives and analyzes the ultrasound echo to generate a tomographic image of inside of the subject. The ultrasound diagnostic apparatus can acquire a two or three dimensional ultrasound image in real time by scanning, in an orientation direction, the ultrasound wave converged to a specific direction. Thus, generating an ultrasound image continuously in the ultrasound diagnostic apparatus enables observation of a moving image of a living body of the subject.

Further, in recent years, in ultrasound diagnostic apparatuses of this type, an apparatus which images both of an ultrasound probe and a subject using a camera and displays, on a monitor, a camera image attached to an ultrasound image so as to allow recognition of a position of the ultrasound probe and a status of a movement of the subject on a display image and/or the like has been studied (for example, see Japanese Patent Application Laid-Open No. 2009-207800 (hereinafter, referred to as "PTL 1")).

Meanwhile, the present inventors have been conducting studies on applying such an ultrasound diagnostic apparatus to observation of a living body part in a living body of the subject, such as a joint, muscle, or a tendon that moves in accordance with a movement of the subject, such as bending and stretching (hereinafter, referred to as "moving living body part").

For example, observing motion of a moving living body part (e.g., a muscle or a tendon) by an ultrasound diagnostic apparatus makes it possible to know mobility of the moving living body part.

However, when an inspector attempts to more accurately inspect the mobility of the moving living body part while imaging an ultrasound image, it is necessary to simultaneously visually recognize both the movement of the subject (e.g., flexion, extension, adduction, abduction) and the ultrasound image. In this regard, in the ultrasound diagnostic apparatus according to the conventional technology, the inspector is required to visually recognize the ultrasound image, while visually recognizing the actual movement of the subject or the camera image being imaged by camera. Consequently, it is hard for the inspector to recognize the linkage between the movement of the subject and the motion of the moving living body part of the subject (i.e., the mobility).

SUMMARY

The present disclosure has been made in view of the above-described problems, and an object thereof is to provide an ultrasound diagnostic apparatus, a control method for ultrasound diagnostic apparatus, and a non-transitory computer-readable recording medium storing control program for ultrasound diagnostic apparatus capable of supporting a dynamic inspection of a moving living body part by an inspector.

To achieve at least one of the abovementioned objects, according to an aspect of the present invention, an ultrasound diagnostic apparatus reflecting one aspect of the present invention includes a hardware processor that:
  generates an ultrasound image of the living body based on a reception signal acquired from an ultrasound probe which transmits and receives an ultrasound;
  detects the movement of the subject by performing an image analysis of time-series camera images acquired from a camera which images the movement of the subject; and
  generates a display image including the ultrasound image, and changes a display content or display mode of the display image in conjunction with the movement of the subject detected by the image analysis.

To achieve at least one of the abovementioned objects, according to another aspect of the present invention, a control method for an ultrasound diagnostic apparatus to be applied to an ultrasound inspection of a living body part that moves with a movement of a subject in a living body inside the subject, the control method includes:
  generating an ultrasound image based on a reception signal acquired from an ultrasound probe which transmits and receives an ultrasound;
  detecting a movement of the subject by performing an image analysis of time-series camera images acquired from a camera which images the movement of the subject; and
  generating a display image including the ultrasound image, and changing a display content or display mode of the display image in conjunction with the movement of the subject detected by the image analysis.

To achieve at least one of the abovementioned objects, according to another aspect of the present invention, a non-transitory computer-readable recording medium storing a control program for an ultrasound diagnostic apparatus to be applied to an ultrasound inspection of a living body part that moves with a movement of a subject in a living body inside the subject, the control program causing the ultrasound diagnostic apparatus to perform:
  generating an ultrasound image based on a reception signal acquired from an ultrasound probe which transmits and receives an ultrasound;
  detecting a movement of the subject by performing an image analysis of time-series camera images acquired from a camera which images the movement of the subject; and
  generating a display image including the ultrasound image, and changing a display content or display mode of the display image in conjunction with the movement of the subject detected by the image analysis.

BRIEF DESCRIPTION OF DRAWINGS

The advantages and features provided by one or more embodiments of the invention will become more fully understood from the detailed description given hereinbelow and the appended drawings which are given by way of illustration only, and thus are not intended as a definition of the limits of the present invention.

DETAILED DESCRIPTION OF EMBODIMENTS

Hereinafter, one or more embodiments of the present invention will be described with reference to the drawings. However, the scope of the invention is not limited to the disclosed embodiments.

Preferred embodiments of the present invention will be described in detail with reference to the attached drawings. Note that, elements having substantially the same functions are assigned the same reference numerals in the description and drawings to omit duplicated descriptions thereof.

First Embodiment

[Entire Configuration of Ultrasound Diagnostic Apparatus]

A description will be given of an entire configuration of ultrasound diagnostic apparatus according to the first embodiment of the present invention with reference to FIGS. 1 to 5.

Figure 1:
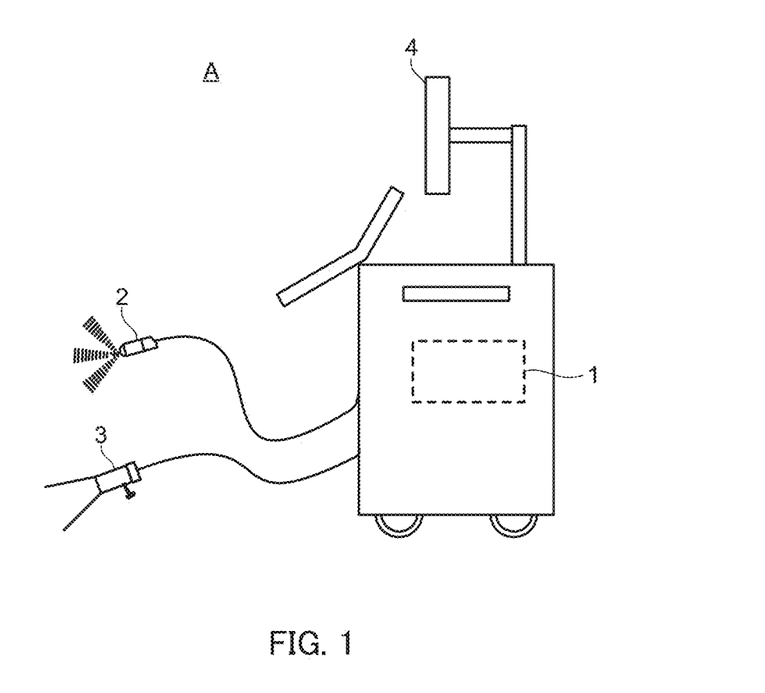
FIG. 1 illustrates a configuration of an ultrasound diagnostic apparatus according to a first embodiment.

FIG. 1 illustrates a configuration of ultrasound diagnostic apparatus A according to the present embodiment.

Ultrasound diagnostic apparatus A includes image processing device 1, ultrasound probe 2, camera 3, and monitor 4. Note that, image processing device 1 is incorporated in a main body of ultrasound diagnostic apparatus A. Further, ultrasound probe 2 and camera 3 are connected to the main body of ultrasound diagnostic apparatus A (image processing device 1) via cables, respectively.

Ultrasound probe 2 transmits an ultrasound beam (here, approximately 1 to 30 MHz) into subject P1 (e.g., a human body) and functions as an acoustic sensor that receives an ultrasound echo reflected in subject P1 of the transmitted ultrasound beam to convert the received ultrasound echo into an electric signal.

Ultrasound probe 2 is configured to include transducer arrays (e.g., piezoelectric element arrays) which are, for example, arranged in an array, and a channel switching section (e.g., a multiplexer) for switching control between on and off of the driving states of each transducer of the transducer arrays individually or on a block basis. Each transducer of ultrasound probe 2 converts a voltage pulse generated by a main body (a transmission circuit, not illustrated) of ultrasound diagnostic apparatus A into an ultrasound beam, transmits the ultrasound beam into a subject, receives an ultrasound echo reflected in the subject, converts the ultrasound echo into an electric signal (hereinafter, referred to as "reception signal"), and outputs the reception signal to image processing device 1. Accordingly, transducers to be driven of ultrasound probe 2 are sequentially switched along a scanning direction, and thus, an ultrasound scanning inside the subject is performed.

Camera 3 is, for example, a general visible camera that performs Analog-to-Digital conversion of an image signal generated by its own imaging element to generate image data relating to a camera image (hereinafter, referred to as a "camera image"). Camera 3 then continuously generates camera images in frame units and outputs the camera images arranged in time series (i.e., a moving image) to image processing device 1.

Camera 3 is placed at an appropriate position around the subject so as to image a movement of the subject (i.e., motion for observation of a moving living body part of an inspection target). Additionally, camera 3 is preferably placed at a place where ultrasound probe 2 is imaged with the subject so as to grasp a pressed state of ultrasound probe 2 to the subject (e.g., a position and/or posture of ultrasound probe 2) from the camera image. Meanwhile, by detecting a position of ultrasound probe 2, an imaging direction and/or imaging position of camera 3 may be automatically adjusted base on the detected position of ultrasound probe 2. (e.g., see PTL 1).

Image processing device 1 generates an ultrasound image based on a reception signal acquired from ultrasound probe 2. Image processing device 1 then adds, for example, the camera image generated by camera 3 to the ultrasound image to generate a display image to be displayed on monitor 4.

Image processing device 1 is mainly configured of, for example, a well-known microcomputer having a Central Processing Unit (CPU), a read-only memory (ROM), and a random access memory (RAM) and the like. In addition, image processing device 1 further incudes, for example, a detection circuit that performs reception processing of the reception signal acquired from ultrasound probe 2 and cine-memory to store a time-series ultrasound image and a time-series camera image. Note that, some or all of the functions of image processing device 1 may be, of course, realized only by a dedicated hardware circuit (e.g., an Application Specific Integrated Circuit (ASIC) or a Field-Programmable Gate Array (FPGA)) not having the CPU and the like.

Monitor 4 is a display that displays a display image generated by image processing device 1 and, for example, configured of a liquid crystal display.

[Configuration of Image Processing Device]

Figure 2:
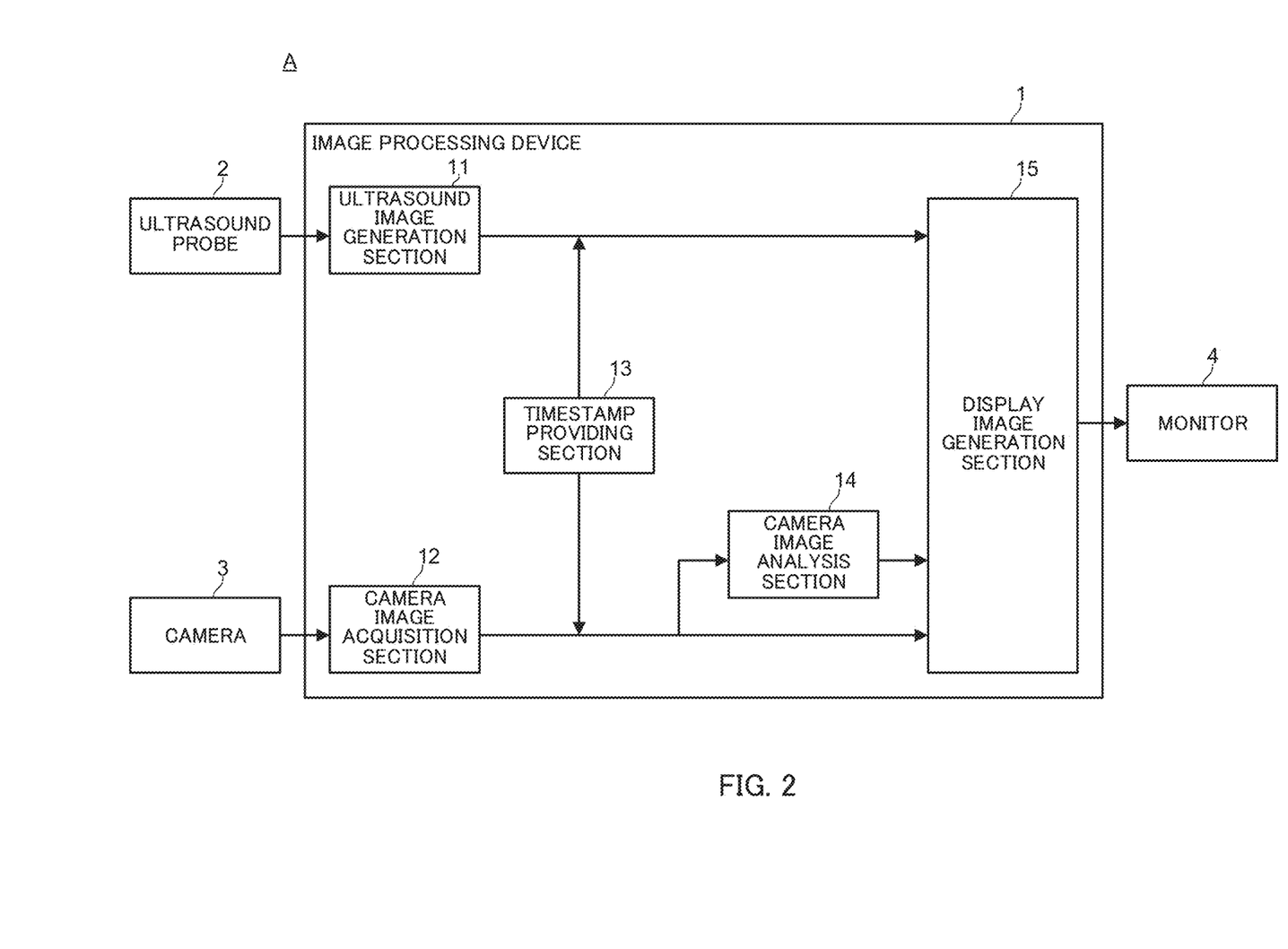
FIG. 2 illustrates a configuration of an image processing device of the ultrasound diagnostic apparatus according to the first embodiment.

FIG. 2 illustrates a configuration of image processing device 1 of ultrasound diagnostic apparatus A according to the present embodiment.

Image processing device 1 includes ultrasound image generation section 11, camera image acquisition section 12, timestamp providing section 13, camera image analysis section 14, and display image generation section 15.

Ultrasound image generation section 11 acquires the reception signal related to the ultrasound echo from ultrasound probe 2 and generates the ultrasound image (i.e., a tomographic image) of the inside of subject P1. For example, ultrasound image generation section 11 continuously accumulates, in a line memory, the signal intensities (Intensity) of an ultrasound echo detected after ultrasound probe 2 transmits a pulsed ultrasound beam in the depth direction. Along with the ultrasound beam from ultrasound probe 2 is scanned across the inside of the subject, ultrasound image generation section 11 continuously accumulates the signal intensities of the ultrasound echo at each scanning position in each line memory, to thereby generate two-dimensional data in frame units. Ultrasound image generation section 11 then generates an image data related to the ultrasound image (hereinafter, abbreviated as an "ultrasound image") by converting, into a brightness value, the intensities of the ultrasound echo detected at each position of the inside of the subject.

Ultrasound image generation section 11 continuously generates the ultrasound image in the frame rate corresponding to scanning speed of ultrasound probe 2.

Camera image acquisition section 12 sequentially acquires the continuously generated camera image from camera 3. Camera image acquisition section 12 sequentially acquires the camera image, for example, at intervals of the frame rate in which the camera image is generated in camera 3.

Timestamp providing section 13 provides a timestamp to an ultrasound image, when ultrasound image generation section 11 generates the ultrasound image. In addition, timestamp providing section 13 provides a timestamp to a camera image when camera image acquisition section 12 acquires the camera image. A time of the timestamp provided to the ultrasound image and a time of the timestamp provided to the camera image individually indicate the time when each data is generated.

A frame rate for generating an ultrasound image by ultrasound image generation section 11 is usually different from a frame rate for generating a camera image by camera 3. Thus, in the present embodiment, a correspondence relation between a generation timing of the ultrasound image and a generation timing of the camera image can be identified by the times of the timestamps that timestamp providing section 13 provides to the ultrasound image and the camera image, respectively.

Camera image analysis section 14 performs an image analysis of a time-series camera image acquired from camera image acquisition section 12 to detect a movement of the subject. Camera image analysis section 14 then transmits information on the detected movement of the subject to display image generation section 15. Note that, the movement of the target subject to be detected by camera image analysis section 14 is a motion of a moving part (e.g., finger, arm, knee, shoulder, ankle) of the subject (hereinafter, simply referred to as a "subject movement") linkage with a moving living body part of the target to be observed in an ultrasound image.

Camera image analysis section 14 detects the subject movement by, for example, detecting a moving part of the subject from each frame of the camera image arranged in time series and tracking the moving part. Any method can be used by camera image analysis section 14 for detecting the moving part; therefore, camera image analysis section 14 may detect the moving part by using pattern matching such as template matching. Note that, in a case where a marker for tracking is mounted on the subject, camera image analysis section 14 may track the moving part according to a position of the marker.

Meanwhile, information on the subject movement to be output by camera image analysis section 14 can be in any format. For example, the information may be information on a position of a moving part (e.g., a position of each joint of the moving part) in each frame of the camera image arranged in time series. Additionally, the information may be information on a vector indicating a temporal variation of the position of the moving part. Furthermore, the information may be information on a classification result indicating which of a plurality of motions classified in advance the detected subject movement corresponds to.

Display image generation section 15 acquires an ultrasound image from ultrasound image generation section 11 and also acquires a camera image from camera image acquisition section 12 to generate a display image in which the ultrasound image and the camera image are embedded. Display image generation section 15 then transmits the generated display image data to monitor 4 to display the display image. Thus, display image generation section 15 updates the display image sequentially and displays the display image in a moving image format on monitor 4.

Note that, at this time, display image generation section 15 identifies a temporal correspondence relation between a generation timing of the ultrasound image and a generation timing of the camera image, based on, for example, the time of a timestamp provided to the ultrasound image and the time of a timestamp provided to the camera image; and thereby, display image generation section 15 generates a display image including the ultrasound image and the camera image which are generated at the same or close timing.

Figure 3:
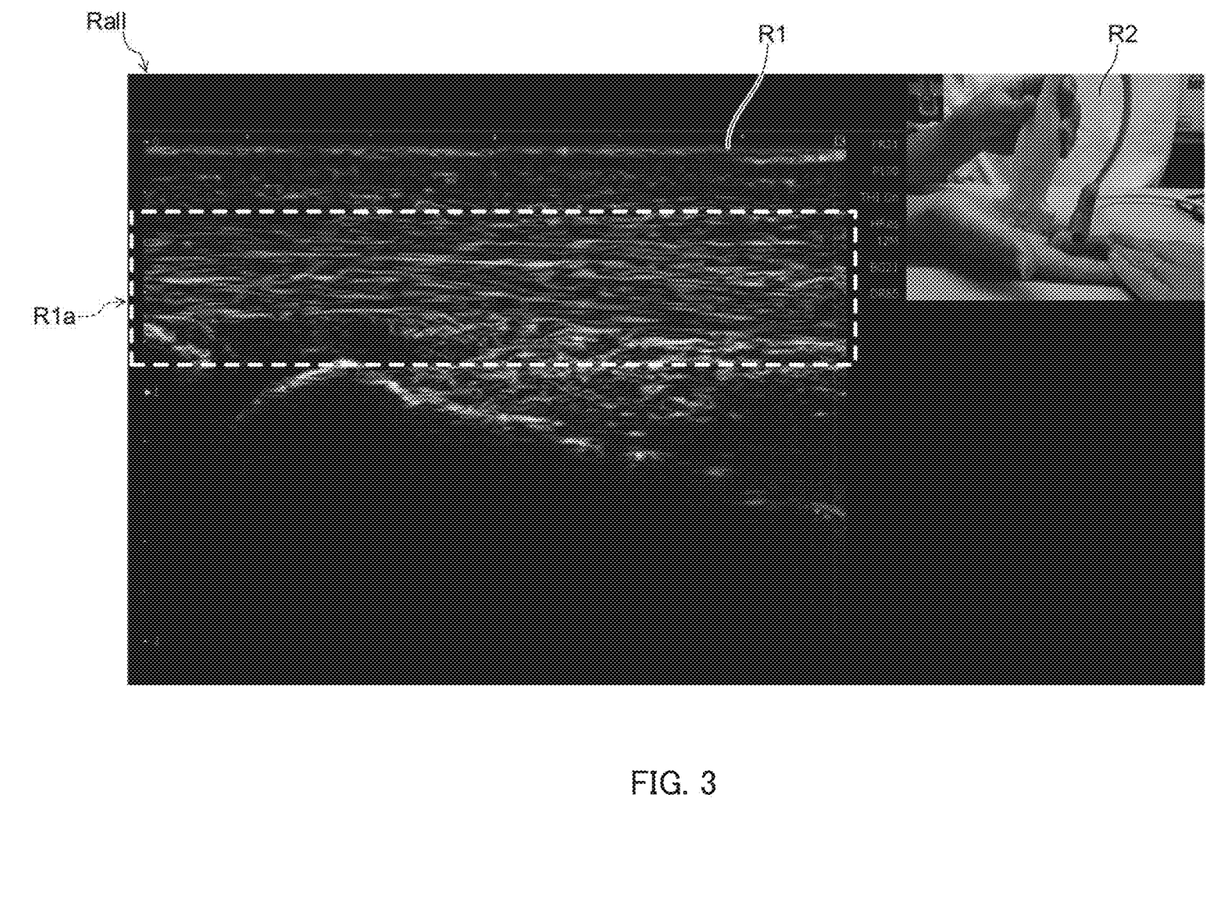
FIG. 3 illustrates an exemplary display image that is generated by a display image generation section according to the first embodiment.

FIG. 3 illustrates an exemplary display image that is generated by display image generation section 15 according to the present embodiment. In FIG. 3, R all represents the entire display image, R1 represents an ultrasound image, and R2 represents a camera image. In addition, R1a of ultrasound image R1 corresponds to a region in which a moving living body part (here, finger flexor tendon) is imaged. Note that, FIG. 3 is a display image of when the subject does not move; and a support image described below will be added to the display image when the subject moves.

FIG. 3 presents a situation in which an inspection is executed to evaluate a mobility of a finger flexor tendons. In this inspection, for example, the subject bends the finger under a situation in which an ultrasound image of the finger flexor tendon is continuously imaged while ultrasound probe 2 is pressed to near the base of the finger of the subject. Then, at this time, from the movement mode of the moving living body part R1a reflected in ultrasound image R1, the evaluation of the mobility of the finger flexor tendon is performed. It is said that, in the normal case, the finger flexor tendon moves to the left and right when the subject bends the finger, but in the abnormal case, the finger flexor tendon adheres to surrounding tissues, and the movement mode becomes slow (i.e., a state in which hooking occurs) as compared with the movement of the finger.

Here, for the purpose of supporting a mobility inspection of the moving living body part by the subject, display image generation section 15 has a function of adding, in the display image, information relating to the subject movement or information relating to the motion of the moving living body part (in the present embodiment, information relating to the subject movement) (hereinafter, also referred to as "support image"), and changing display contents or a display mode of the information in conjunction with the subject movement detected by camera image analysis unit 14.

As described above, in the ultrasound diagnostic apparatus according to the conventional technology, an inspector is required to visually recognize the ultrasound image, while visually recognizing the actual subject movement or the camera image being imaged by camera 3. Consequently, it is hard for the inspector to recognize the mobility of the moving living body part (i.e., the linkage between the subject movement and the motion of the moving living body part of the subject). In ultrasound diagnostic apparatus A according to the present embodiment, display image generation section 15 has the function in order to solve such a problem.

Figure 4:
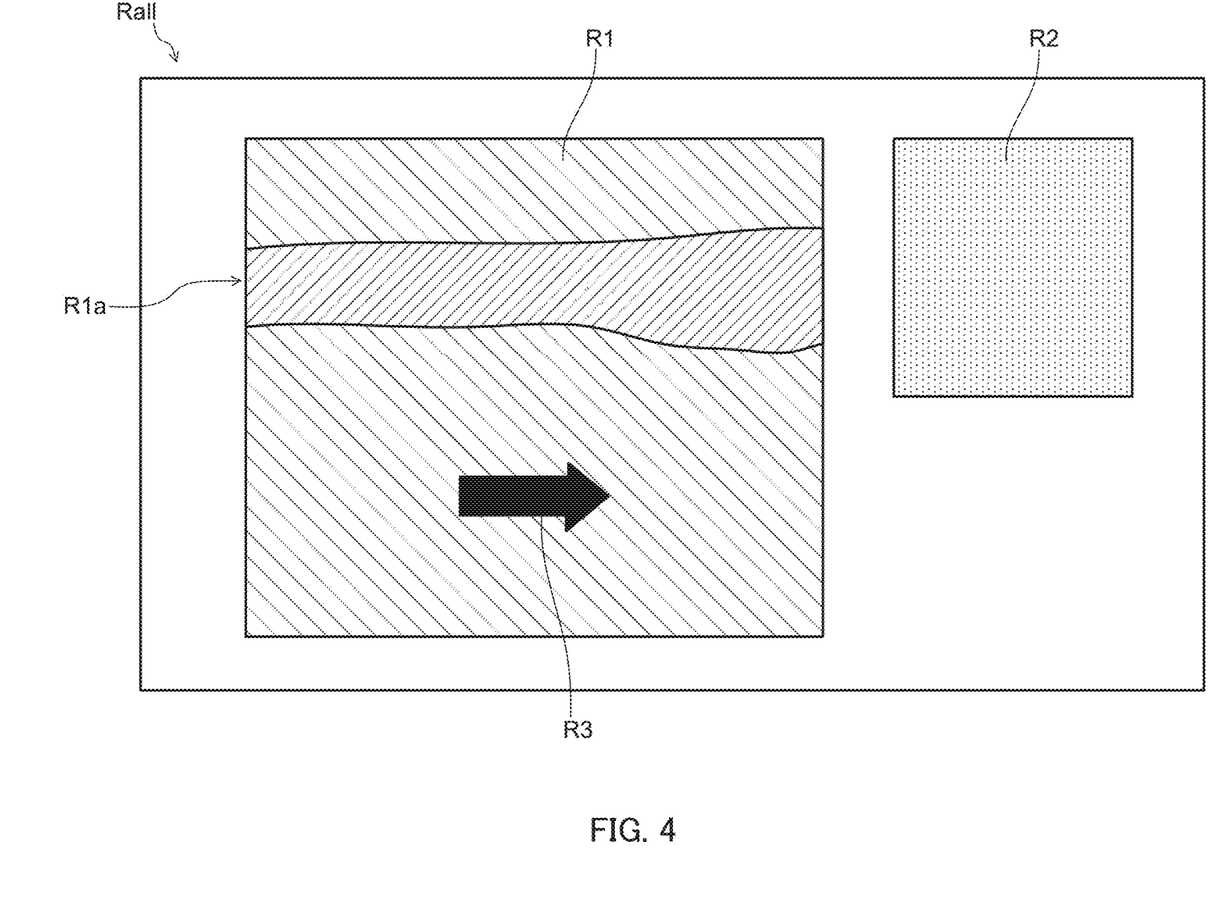
FIG. 4 illustrates an exemplary support image that is generated by the display image generation section according to the first embodiment.

FIG. 4 illustrates an exemplary support image (R3 in FIG. 4) that is generated by display image generation section 15 according to the present embodiment. FIG. 4 is display image Rall corresponding to FIG. 3, and, for convenience of description, ultrasound image R1 and camera image R2 are not illustrated in FIG. 4.

"Support image" is, for example, an image illustrating the movement direction of the moving part of the subject. FIG. 4, as an exemplary "support image", illustrates arrow image R3 which is linked with a subject movement to bend the finger. When the subject bends the finger, in the normal case, the finger flexor tendon (the moving living body part R1*a* in ultrasound image R1) moves to the right in the ultrasound image. Hence, in FIG. 4, since the subject has performed the movement to bend the finger, right arrow image R3 is added as a support image.

This allows the inspector to evaluate normality (i.e., the linkage between the subject movement and the movement of the moving living body part) of the motion of the moving living body part (here, the finger flexor tendon) without paying attention to the actual subject movement, while only viewing the display image (in particular, the ultrasound image). From the viewpoint of improving visibility of the support image, the support image is preferably displayed at a superimposed/or adjacent position on/to the ultrasound image.

Image data of the "support image", for example, in the ROM or the like of image processing device 1, is stored for each moving part, in advance, in association with the moving mode of the moving part. For example, when the moving part is a finger, as in FIG. 4, the finger flexor tendon is displayed to extend laterally in the ultrasound image, and has a characteristic to move left and right when the subject bends the finger, and thus, data of support image R3 is registered as an image of a right or left arrow. Thus, display image generating unit 15 reads the data of the support image from the ROM or the like of image processing device 1 and generates a display image to which the support image is added so as to superimpose the support image on the ultrasound image, based on, for example, information on the moving part set in advance and the analysis result of camera image analysis section 14.

The "support image" may be, for example, an image indicating only the moving direction of the moving part of the subject; however, is preferable to be an image indicating a movement variation per unit time of the moving part of the subject (i.e., movement speed) together with a direction of the movement. In this case, the "support image" may have, for example, different length, thickness, or color or the like of arrow indicating the movement direction of the moving part of the subject depending on the movement speed of the moving part of the subject. This makes it possible to more clearly suggest the linkage between the subject movement and the motion of the moving living body part using the support image.

Further, the "support image" is preferably displayed in order to recognize the timing when the subject changes the movement direction of the moving part. For example, in the aspect of FIG. 4, display image generation section 15 preferably changes a direction of arrow image R3 when the subject has changed the movement direction of the moving part. This allows the inspector to more easily recognize the linkage between the subject movement and the motion of the moving living body part of the subject.

Figure 5:
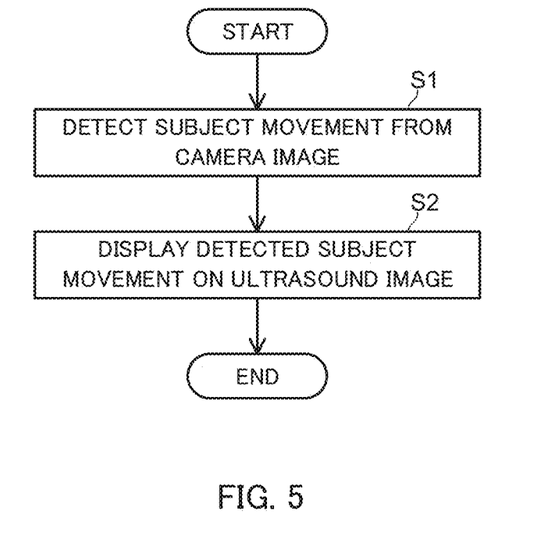
FIG. 5 is a flowchart illustrating an exemplary operation of the image processing device according to the first embodiment.

FIG. 5 is a flowchart illustrating an exemplary operation of image processing device 1 according to the present embodiment. FIG. 5 illustrates only a procedure performed by image processing device 1 to generate a support image. Note that, the flowchart illustrated in FIG. 5 is, for example, a procedure to be repeatedly performed by image processing device 1 at predetermined intervals (e.g., in frame units for generating a display image) according to a computer program.

Firstly, image processing device 1 (camera image analysis section 14) performs an image analysis of a camera image to detect a subject movement, based on the analysis result (step S1). Then, image processing device 1 (display image generation section 15) adds a support image indicating the subject movement detected in step S1 to a position for superimposing on an ultrasound image in a display image (step S2).

Display image generation section 15 can display the support image on the ultrasound image in order to link with the subject movement by repeatedly performing such a process.

As described above, ultrasound diagnostic apparatus A according to the present embodiment allows an inspector to easily recognize the linkage between a subject movement and a motion of a moving living body part of the subject (i.e., mobility of the moving living body part).

Second Embodiment

Next, a description will be given of a configuration of ultrasound diagnostic apparatus A according to the second embodiment with reference to FIGS. 6 to 8. Ultrasound diagnostic apparatus A according to the present embodiment is different from ultrasound diagnostic apparatus A according to the first embodiment in adding, to a display image, information related to strength of motion correlation between a subject movement and a motion of a moving living body part of the subject. Note that, a description of configuration common to the first embodiment is omitted (hereinafter, the same applies to the other embodiments).

Figure 6:
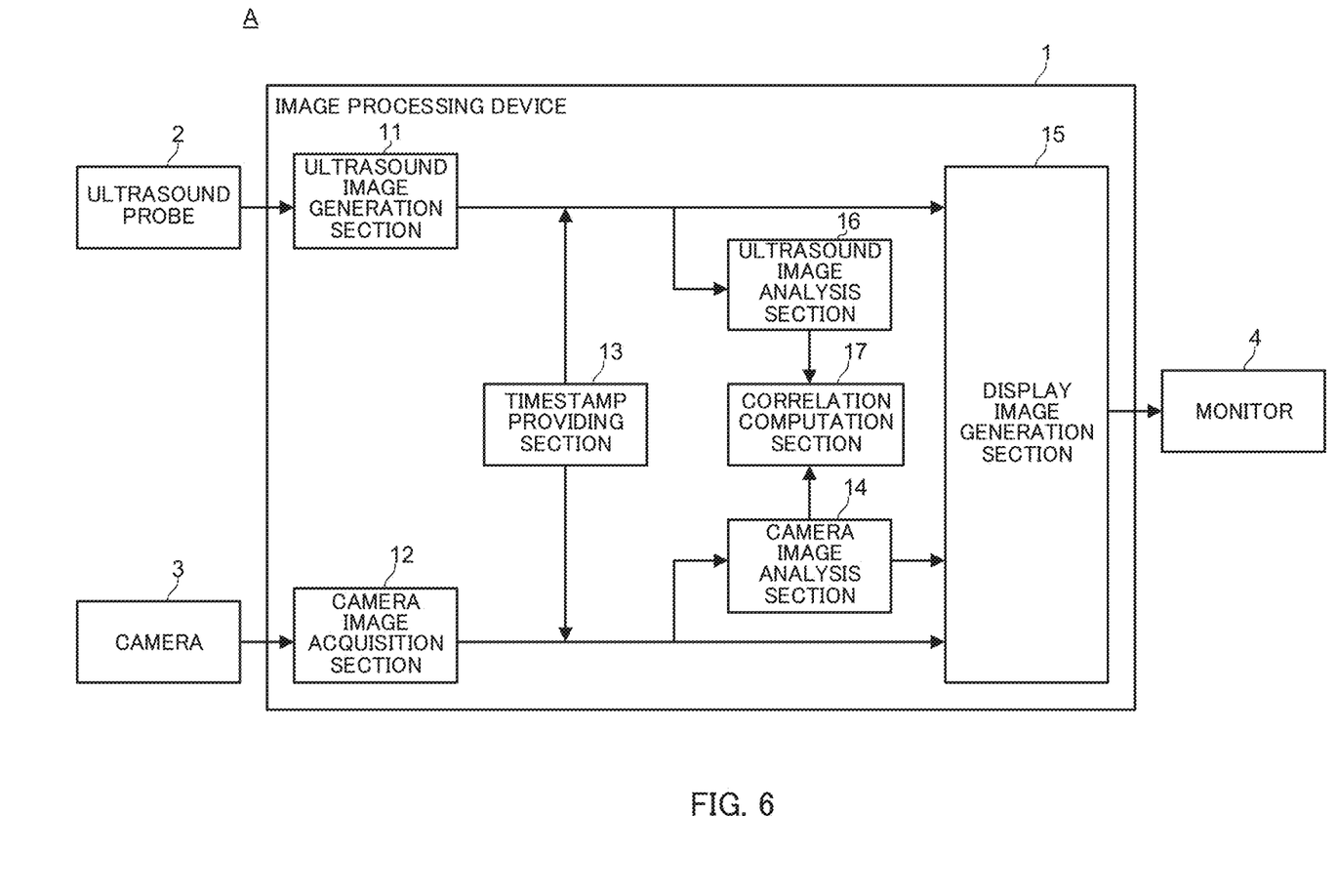
FIG. 6 illustrates a configuration of an image processing device of an ultrasound diagnostic apparatus according to a second embodiment.

FIG. 6 illustrates a configuration of image processing device 1 of ultrasound diagnostic apparatus A according to the second embodiment.

Image processing device 1 according to the present embodiment includes ultrasound image generation section 11, camera image acquisition section 12, timestamp providing section 13, camera image analysis section 14, display image generation section 15, and in addition, ultrasound image analysis section 16 and correlation computation section 17. Further, in the present embodiment, camera image analysis section 14 is configured to transmit information on the detected subject movement to correlation computation section 17.

Ultrasound image analysis section 16 performs an image analysis of a time-series ultrasound image generated by ultrasound image generation section 11 to detect a motion of a moving living body part of the subject. Ultrasound image analysis section 16 then transmits information on the detected motion of the moving living body part of the subject to correlation computation section 17.

Ultrasound image analysis section 16 identifies the identity of a characteristic point among frames by, for example, performing pattern matching such as template matching. Ultrasound image analysis section 16 then tracks the characteristic point of a portion of a moving living body part and detects a movement of the characteristic point as a motion of the moving living body part.

Note that, as a method for detecting the motion of the moving living body part, ultrasound image analysis section 16 may use a gradient method that estimates a movement destination of each local region by time-space differentiation of a moving image.

Correlation computation section 17 performs correlation computation between the subject movement detected by camera image analysis section 14 and the motion of the moving living body part of the subject detected by ultrasound image analysis section 16, and transmits the operation result to display image generation section 15. A computation method of the correlation computation performed by correlation computation section 17 depend on each expression form of the subject movement and the motion of the moving living body part; for example, correlation computation section 17 performs these correlation computations by using an Euclidean distance or a correlation function and the like.

Display image generation section 15 according to the present embodiment adds, to a display image, an image indicating strength between the subject movement and the motion of the moving living body part of the subject operated by correlation computation section 17, as a support image to support a mobility inspection of the moving living body part.

Figure 7:
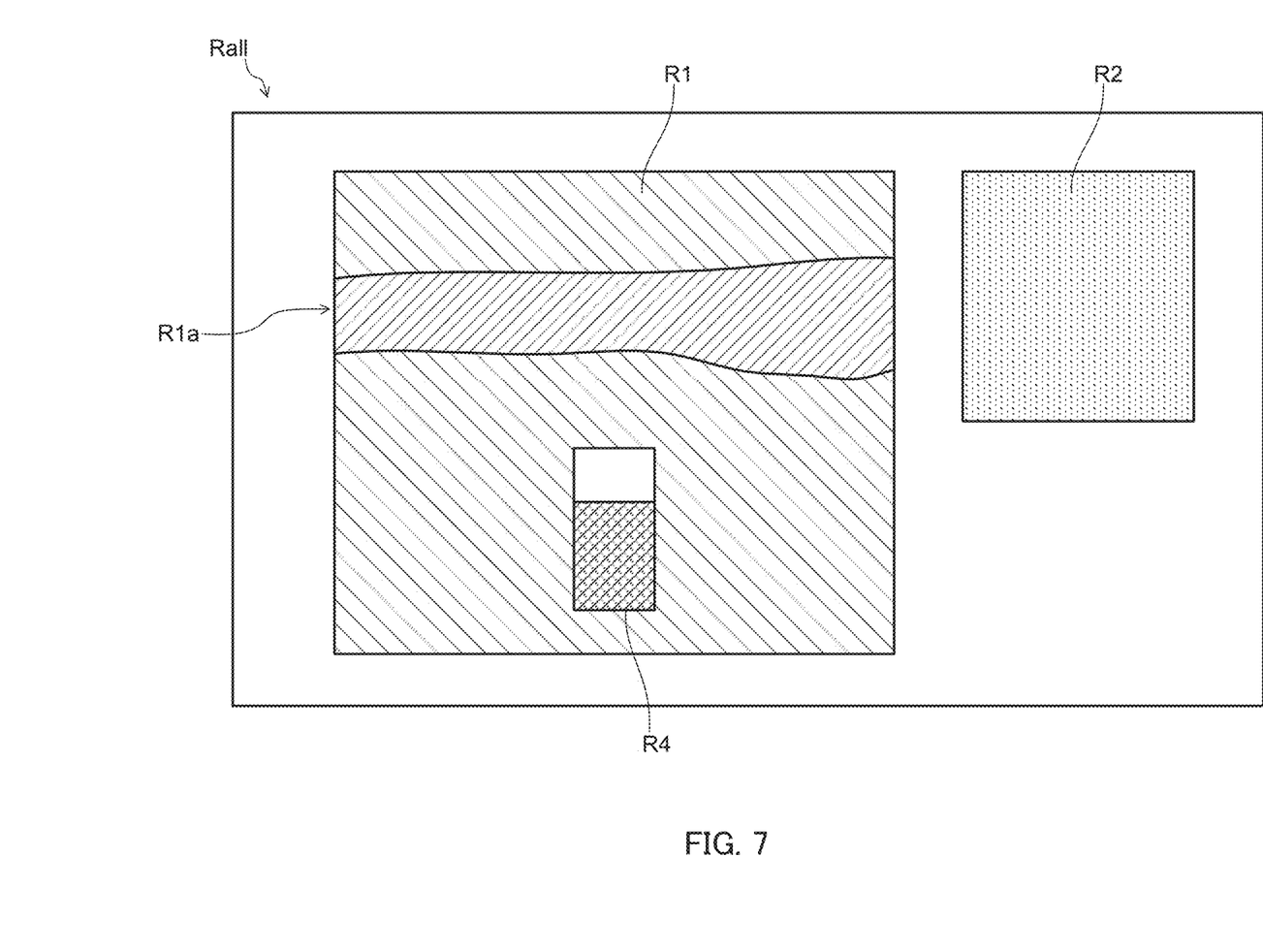
FIG. 7 illustrates an exemplary support image that is generated by a display image generation section according to the second embodiment.

FIG. 7 illustrates an exemplary support image (R4 in FIG. 7) that is generated by display image generation section 15 according to the present embodiment. FIG. 7 is display image corresponding to FIG. 4 referred to in the first embodiment. In the present embodiment, a gauge showing strength of correlation between the subject movement and the motion of the moving living body part of the subject (here, a magnitude of the correlation strength to the complete coincidence, i.e., 100%) is used as support image R4.

Figure 8:
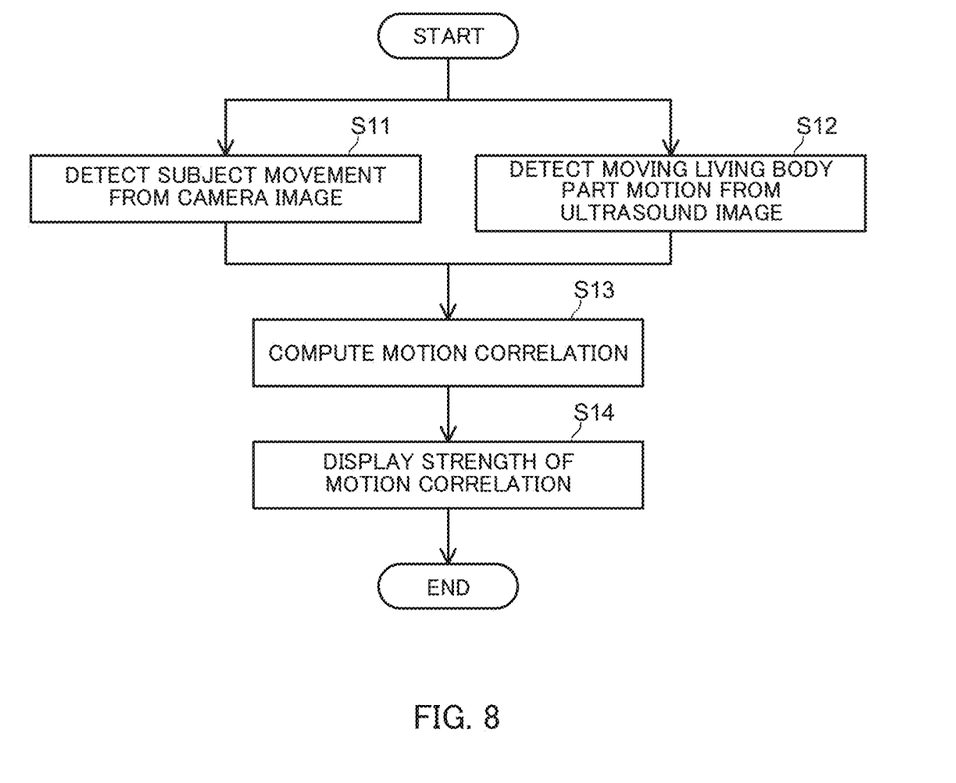
FIG. 8 is a flowchart illustrating an exemplary operation of the image processing device according to the second embodiment.

FIG. 8 is a flowchart illustrating an exemplary operation of image processing device 1 according to the present embodiment. Note that, FIG. 8 illustrates only a procedure performed by image processing device 1 to generate a support image.

Image processing device 1 (camera image analysis section 14) performs an image analysis of a camera image to detect a subject movement (step S11). In addition, in parallel to step S11, image processing device 1 (ultrasound image analysis section 16) performs an image analysis of an ultrasound image to detect a motion of a moving living body part (step S12).

Then, image processing device 1 (correlation computation section 17) performs correlation operation between the subject movement detected in step S11 and the motion of the moving living body part of the subject detected in step S12 (step S13). Image processing device 1 (display image generation section 15) superimposes the support image indicating the strength of correlation, calculated in step S13, between the subject movement and the motion of the moving living body part of the subject on a position where the ultrasound image in the display image is displayed (step S14).

Display image generation section 15 can display the support image indicating the strength of motion correlation between the subject movement and the motion of the moving living body part of the subject in order to link with the subject movement by repeatedly performing such a process.

As described above, ultrasound diagnostic apparatus A according to the present embodiment allows an inspector to easily recognize the linkage between a subject movement and a motion of a moving living body part of the subject (i.e., mobility of the moving living body part). In particular, ultrasound diagnostic apparatus A according to the present embodiment is useful in allowing the inspector to recognize the subject movement and the motion of the moving living body part of the subject from only the support image.

Third Embodiment

Next, a description will be given of a configuration of ultrasound diagnostic apparatus A according to the third embodiment with reference to FIGS. 9 to 11. Ultrasound diagnostic apparatus A according to the present embodiment is different from ultrasound diagnostic apparatus A according to the first embodiment in changing display contents or a display mode of an image related to a motion of a moving living body part to be displayed on a display image by using a subject movement detected from a camera image.

Figure 9:
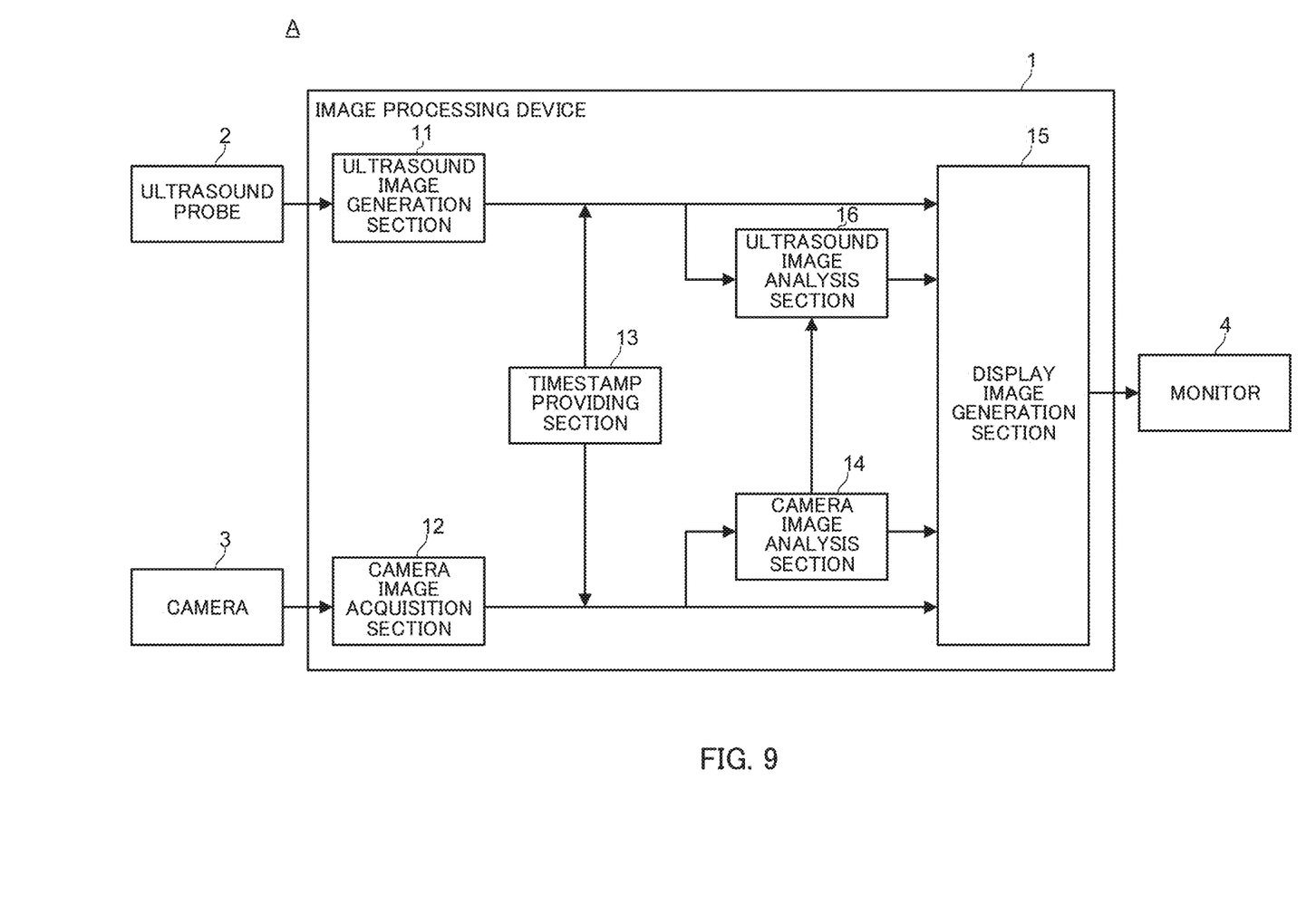
FIG. 9 illustrates a configuration of an image processing device of an ultrasound diagnostic apparatus according to a third embodiment.

FIG. 9 illustrates a configuration of image processing device 1 of ultrasound diagnostic apparatus A according to the third embodiment.

Image processing device 1 according to the present embodiment includes ultrasound image generation section 11, camera image acquisition section 12, timestamp providing section 13, camera image analysis section 14, display image generation section 15, and in addition, ultrasound image analysis section 16.

Ultrasound image analysis section 16 according to the present embodiment performs an image analysis of a time-series ultrasound image generated by ultrasound image generation section 11 and detects a motion of the moving living body part. Ultrasound image analysis section 16 then transmits information on the detected motion of the moving living body part to display image generation section 15.

A detection method and a tracking method of a characteristic point used by ultrasound image analysis section 16 according to the present embodiment are similar to the method used by ultrasound image analysis section 16 according to the second embodiment. Ultrasound image analysis section 16 identifies the identity of a characteristic point among frames by, for example, performing any pattern matching, and thereby tracks the characteristic point of a moving living body part and detects a movement of the characteristic point (i.e., a vector) as a motion of the moving living body part.

Display image generation section 15 according to the present embodiment adds, to a display image, information on the motion of the moving living body part detected by ultrasound image analysis section 16, as a support image to support a mobility inspection of the moving living body part. Display image generation section 15 then changes display contents or a display mode of the support image so that a change timing of a movement direction of a moving part of the subject detected by camera image analysis section 14 is identifiable.

Figure 10:
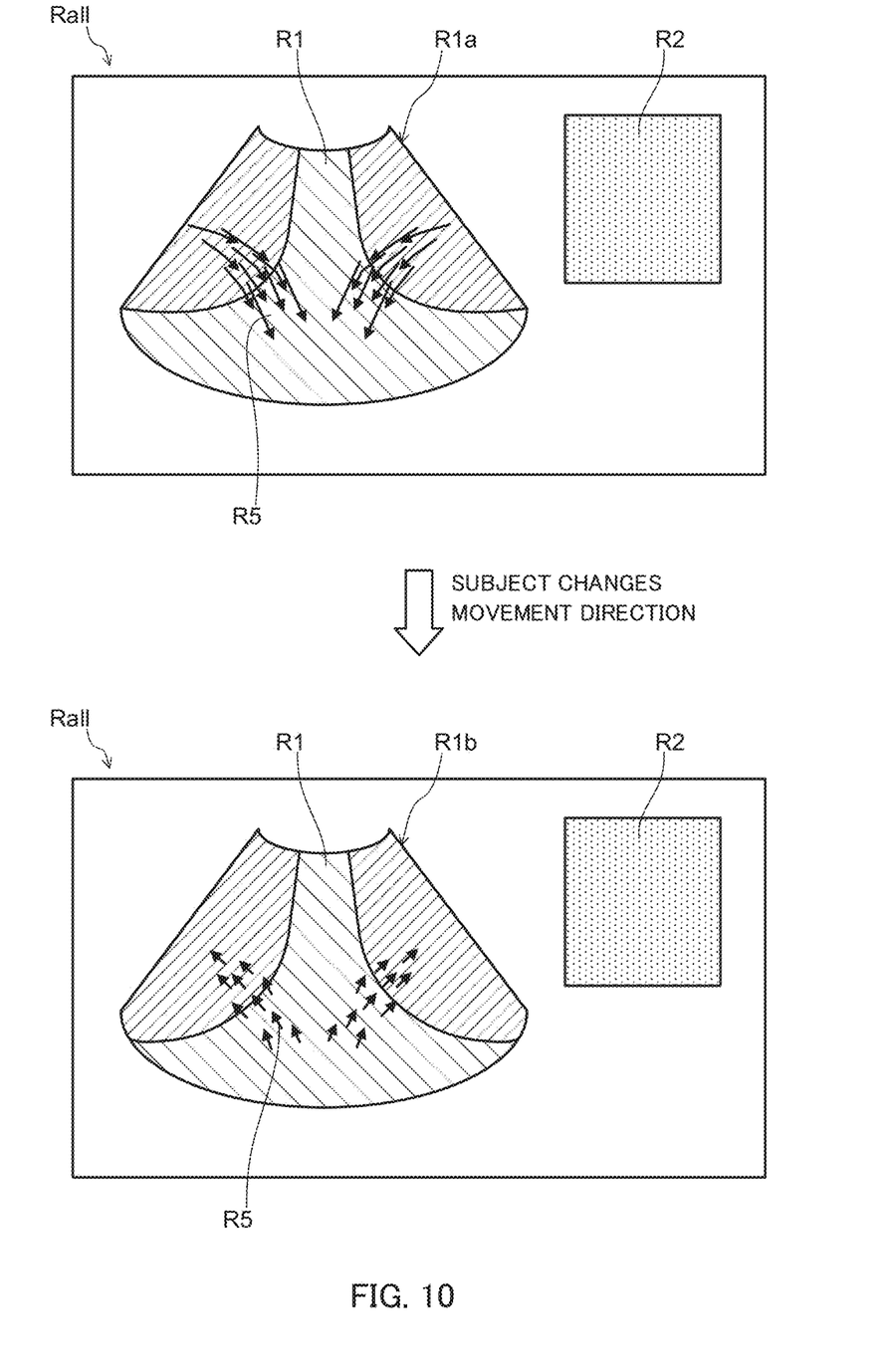
FIG. 10 illustrates an exemplary support image that is generated by a display image generation section according to the third embodiment.

FIG. 10 illustrates an exemplary support image (R5 in FIG. 10) that is generated by display image generation section 15 according to the present embodiment. FIG. 10 is a display image corresponding to FIG. 4 referred to in the first embodiment. Incidentally, FIG. 10 illustrates s a display image to be displayed when an ultrasound inspection of the thigh muscle of the subject (i.e., the moving living body part) is performed. Region R1b of ultrasound image R1 is the thigh muscle of the subject.

The upper image of FIG. 10 is a display image when the subject bends the knee, and the lower image of FIG. 10 is a display image immediately after the subject extends the knee. Note that, thigh muscles have a characteristic that they gradually move downward when the subject flexes the knee and move upward when the subject extends the knee.

Display image generation section 15 according to the present embodiment tracks each characteristic point of each of the plurality of moving living body parts of the subject and displays a vector image indicating a temporal variation in a position of the characteristic point of the tracking target as a support image (R5 in FIG. 10) superimposed on an ultrasound image. Here, while the subject moves the moving part in the same direction, display image generation section 15 displays the temporal variation in the position of the characteristic point of the tracking target as a continuous vector image (see vector image R5 in the upper image of FIG. 10). When the subject has changed the movement direction of the moving part, display image generation section 15 once deletes (i.e., resets) the vector image from the display image and again displays, on the display image, a reversed vector image with the position of the characteristic point of the tracking target at the timing when the movement direction has been changed, as the starting point (see vector image R5 in the lower image of FIG. 10). Display image generation section 15 controls the timing of the deletion and appearance of the vector image at the timing, as a trigger, when the subject changes the movement direction of the moving part detected by camera image analysis section 14.

Meanwhile, for some of moving living body parts of the subject, the followability is slow when the subject changes the movement direction of the moving part. At this time, if the display control of the vector image is executed depending only on the ultrasound image, the visibility of the vector image is deteriorated, such as a mixture of vector images of different directions.

Figure 11:
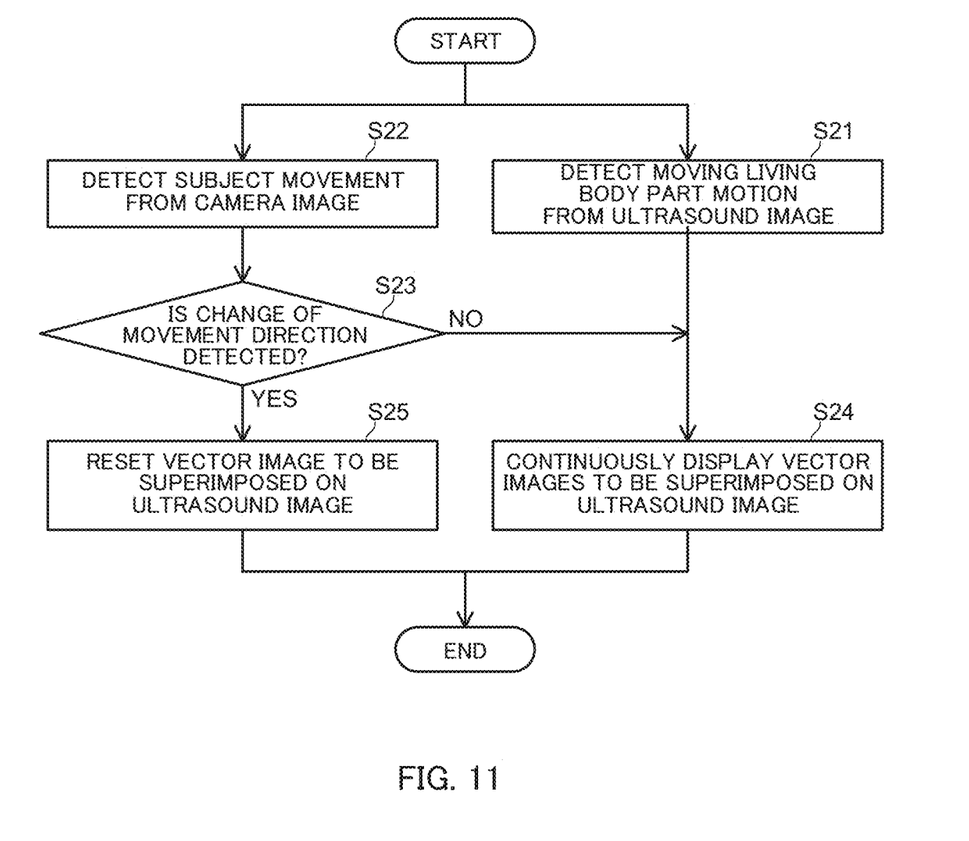
FIG. 11 is a flowchart illustrating an exemplary operation of the image processing device according to the third embodiment.

In this regard, as display image generation section 15 according to the present embodiment, controlling the deletion and appearance of the vector image at the timing when the subject has changed the movement direction of the moving part as a trigger allows the inspector to easily recognize the motion of the moving living body part in conjunction with the change of the subject movement, while visually recognizing only the ultrasound image FIG. 11 is a flowchart illustrating an exemplary operation of image processing device 1 according to the present embodiment. Note that, FIG. 11 illustrates only a procedure performed by image processing device 1 to generate a support image.

Image processing device 1 (ultrasound image analysis section 16) performs an image analysis of an ultrasound image to detect a motion of a moving living body part (step S21). In addition, in parallel to step S21, image processing device 1 (camera image analysis section 14) performs an image analysis of a camera image to detect a subject movement (step S22). Thus, image processing device 1 (display image generation section 15) determines whether the subject has changed a movement direction of moving part based on the subject movement detected in step S22 (step S23).

Image processing device 1 (display image generation section 15) changes a display mode of the vector image representing the motion of the moving living body part based on the determination result in step S23. That is, when adding a vector image representing the motion of the moving living body part detected in step S21 to the display image, image processing device 1 (display image generation section 15) adds the vector image so that the vector image is continuous from the vector image before the moment (step S24), in a case where the movement direction of the moving part of the subject has not been changed (step S23: NO). On the other hand, in a case where the movement direction of the moving part of the subject has been changed (Step S23: YES), image processing device 1 (display image generation section 15) resets (i.e., deletes) the vector image before the moment and adds, to the display image, a reversed vector image with the end position of the characteristic point of the tracking target as the starting point (Step S25).

Display image generation section 15 can switch display contents or a display mode of the support image indicating the motion of the moving living body part, to be displayed on a moving image of the ultrasound image in order to link with the subject movement by repeatedly performing such a process.

As described above, ultrasound diagnostic apparatus A according to the present embodiment allows an inspector to easily recognize the linkage between a subject movement and a motion of a moving living body part of the subject (i.e., mobility of the moving living body part). In particular, ultrasound diagnostic apparatus A according to the present embodiment is useful in allowing the inspector to recognize in detail the motion of the mobility of each portion of moving living body parts from the support image.

Other Embodiments

The present invention is not limited to the above-described embodiments, and various modified modes may be derived from the above-described embodiments.

In each of the above embodiments, as an aspect in which display image generation section 15 realizes a function of supporting the mobility inspection of the moving living body part, an aspect is described in which the following images are switched in conjunction with the subject movement: an image illustrating the movement direction of the moving part of the subject, an image illustrating the strength of the correlation between the subject movement and the motion of the living body part, and an image illustrating the direction of motion of the living body part are changed in conjunction with the subject movement. However, an aspect to realize the function by display image generation section 15 can be changed variously. For example, at normal time only an ultrasound image may be displayed only on the display image, and in a case where the subject movement is detected, a camera image may be added on the display image. In other words, an aspect to realize the function by display image generation section 15 can be any aspect as long as it changes the display content or display mode of the display image in conjunction with the subject movement detected by camera image analysis section 14.

Further, in each of the above embodiments, as an aspect in which display image generation section 15 realizes a function of supporting the mobility inspection of the moving living body part, an aspect is described in which any one of an image illustrating the movement direction of the moving part of the subject, an image illustrating the strength of the correlation between the subject movement and the motion of the living body part, or an image illustrating the direction of motion of the living body part is displayed in the display image. However, two or more of these images may be displayed simultaneously in the display image.

In each of the above embodiments, an aspect in which display image generation section 15 generates a display image which includes an ultrasound image and camera image is described. However, display image generation section 15 may generate a display image which displays only information on the subject movement extracted from the ultrasound image and the camera image.

Although embodiments of the present invention have been described and illustrated in detail, the disclosed embodiments are made for purposes of illustration and example only and not limitation. The scope of the present invention should be interpreted by terms of the appended claims.

INDUSTRIAL APPLICABILITY

According to an ultrasound diagnostic apparatus of the present invention, it is possible to support a dynamic inspection of a moving living body part by an inspector.

What is claimed is:

1. An ultrasound diagnostic apparatus to be applied to an ultrasound inspection of an internal living body part of a subject, wherein the internal living body part moves with a movement of the subject, the ultrasound diagnostic apparatus comprising a hardware processor that:
    generates an ultrasound image of the internal living body part based on a reception signal acquired from an ultrasound probe which transmits and receives an ultrasound;
    detects the movement of the subject by performing an image analysis of time-series camera images acquired from a camera which images the movement of the subject; and
    generates a display image including the ultrasound image, and changes a display content or display mode of the display image in conjunction with a current movement of the subject detected by the image analysis, wherein the display content or display mode to be changed is an indication on the display image of a movement of the internal living body part with the current movement of the subject detected by the image analysis.

2. The ultrasound diagnostic apparatus according to claim 1, wherein
    the indication is a support image related to the movement of the subject or a motion of the internal living body part on the display image, and the hardware processor changes a display content or display mode of the support image in conjunction with the current movement of the subject detected by the image analysis.

3. The ultrasound diagnostic apparatus according to claim 2, wherein
    the support image includes an image indicating a movement direction of a moving part of the subject.

4. The ultrasound diagnostic apparatus according to claim 2, wherein
    the support image includes an image indicating a movement speed of a moving part of the subject.

5. The ultrasound diagnostic apparatus according to claim 4, wherein
    a length, a thickness, or a color of the support image changes based on the movement speed of the current movement of the subject.

6. The ultrasound diagnostic apparatus according to claim 2, wherein
    the support image includes an image indicating a strength of a correlation between the movement of the subject and of the motion of the internal living body part.

7. The ultrasound diagnostic apparatus according to claim 2, wherein
    the support image includes an image indicating a direction of the motion of the internal living body part.

8. The ultrasound diagnostic apparatus according to claim 2, wherein
    the support image includes an image indicating a direction of a motion of each portion of the internal living body part.

9. The ultrasound diagnostic apparatus according to claim 2, wherein
    the hardware processor changes the display content or display mode of the support image so that a timing when the subject has changed a movement direction of a moving part is identifiable.

10. The ultrasound diagnostic apparatus according to claim 2, wherein
    the support image is added to and superimposed on the ultrasound image.

11. The ultrasound diagnostic apparatus according to claim 1, wherein
    the display image further includes at least one of the camera images.

12. The ultrasound diagnostic apparatus according to claim 11, wherein
    the hardware processor provides a timestamp to the ultrasound image when generating the ultrasound image and provides a timestamp to the camera image when acquiring the camera image from the camera, and
    the hardware processor identifies a temporal correspondence relation between a generation timing of the ultrasound image and a generation timing of the camera image based on a time of the timestamp provided to the ultrasound image and a time of the timestamp provided to the camera image.

13. The ultrasound diagnostic apparatus according to claim 1, wherein
    the hardware processor further performs an image analysis of the ultrasound image of time-series to detect a motion of the internal living body part.

14. The ultrasound diagnostic apparatus according to claim 1, wherein
    the internal living body part is a joint part, a muscle part, or a tendon part.

15. The ultrasound diagnostic apparatus according to claim 1, wherein the display content or display mode to be changed indicates a movement direction of the internal living part based on the current movement of the subject detected by the image analysis or a motion correlation between the current movement of the subject and a movement of the internal body part.

16. A control method for an ultrasound diagnostic apparatus to be applied to an ultrasound inspection of an internal living body part of a subject, wherein the internal living body part moves with a movement of the subject, the control method comprising:

generating an ultrasound image of the internal living body part based on a reception signal acquired from an ultrasound probe which transmits and receives an ultrasound;

detecting a movement of the subject by performing an image analysis of time-series camera images acquired from a camera which images the movement of the subject; and generating a display image including the ultrasound image, and changing a display content or display mode of the display image in conjunction with a current movement of the subject detected by the image analysis, wherein the display content or display mode to be changed is an indication on the display image of a movement of the internal living body part with the current movement of the subject detected by the image analysis.

17. A non-transitory computer-readable recording medium storing a control program for an ultrasound diagnostic apparatus to be applied to an ultrasound inspection of an internal living body part of a subject, wherein the internal living body part that moves with a movement of the subject, the control program causing the ultrasound diagnostic apparatus to perform:

generating an ultrasound image of the internal living body part based on a reception signal acquired from an ultrasound probe which transmits and receives an ultrasound;

detecting a movement of the subject by performing an image analysis of time-series camera images acquired from a camera which images the movement of the subject; and generating a display image including the ultrasound image, and changing a display content or display mode of the display image in conjunction with a current movement of the subject detected by the image analysis, wherein the display content or display mode to be changed is an indication on the display image of a movement of the internal living body part with the current movement of the subject detected by the image analysis.

* * * * *